(12) United States Patent
Liu et al.

(10) Patent No.: US 6,451,291 B1
(45) Date of Patent: Sep. 17, 2002

(54) SURFACTANT SYSTEM FOR INCREASING DENTAL TISSUE ANTIBACTERIAL AGENT UPTAKE

(75) Inventors: Xiaoyan Liu, Highland Park, NJ (US); Malcolm Williams, Piscataway, NJ (US); Ravi Subramanyam, Belle Mead, NJ (US)

(73) Assignee: Colgate Palmolive Company, New York, NY (US)

( * ) Notice: Subject to any disclaimer, the term of this patent is extended or adjusted under 35 U.S.C. 154(b) by 0 days.

(21) Appl. No.: 09/686,639

(22) Filed: Oct. 11, 2000

(51) Int. Cl.$^7$ .................................................. A61K 7/16
(52) U.S. Cl. .......................................................... 424/49
(58) Field of Search ...................... 424/49–58

(56) References Cited

U.S. PATENT DOCUMENTS

| 5,292,502 A | * | 3/1994 | Burke et al. | 424/54 |
| 5,316,758 A | * | 5/1994 | Morishima et al. | 424/54 |
| 5,628,985 A | * | 5/1997 | Stiller et al. | 424/49 |
| 5,646,100 A | * | 7/1997 | Haugk et al. | 510/131 |
| 5,681,548 A | * | 10/1997 | Esposito et al. | 424/49 |
| 5,690,911 A | * | 11/1997 | Mirajkar et al. | 424/49 |
| 5,833,956 A | * | 11/1998 | Gorlin et al. | 424/49 |
| 5,883,059 A | * | 3/1999 | Furman et al. | 520/130 |
| 6,090,772 A | * | 7/2000 | Kaiser et al. | 520/388 |
| 6,096,702 A | * | 8/2000 | Ramirez et al. | 510/421 |
| 6,235,268 B1 | * | 5/2001 | Scherl et al. | 424/49 |
| 6,283,336 B1 | * | 9/2001 | Dwyer et al. | 222/190 |

FOREIGN PATENT DOCUMENTS

| DE | 19522750 | 1/1997 | A61K/7/18 |
| EP | 0692246 | 1/1996 | A61K/7/22 |
| EP | 0867174 | 9/1998 | A61K/7/16 |
| WO | 0162212 | 8/2001 | A61K/7/00 |

* cited by examiner

Primary Examiner—Shep K. Rose
(74) Attorney, Agent, or Firm—Paul Shapiro

(57) ABSTRACT

An oral composition comprising in an orally acceptable vehicle, an effective antiplaque amount of an halogenated diphenyl ether or phenolic antibacterial compound, and an amount of an mixed anionic/zwitterionic surfactant system which is effective to increase the uptake of the antibacterial compound to dental tissue so as to enhance the therapeutic efficacy of the administered antibacterial compound.

8 Claims, No Drawings

SURFACTANT SYSTEM FOR INCREASING DENTAL TISSUE ANTIBACTERIAL AGENT UPTAKE

BACKGROUND OF THE INVENTION

1. Field of the Invention

The present invention relates to an oral composition containing an antibacterial compound for the inhibition of bacterial plaque accumulation on dental tissue and more particularly to an oral composition containing an antibacterial compound and a mixed anionic/zwitterionic surfactant system which promotes significantly higher uptake of the antibacterial compound on dental tissue.

2. The Prior Art

Dental plaque is a soft deposit which forms on teeth and is comprised of an accumulation of bacteria and bacterial by-products. Plaque adheres tenaciously at the points of irregularity or discontinuity, e.g., on rough calculus surfaces, at the gum line and the like. Besides being unsightly, plaque is implicated in the occurrence of gingivitis and other forms of periodontal disease.

A wide variety of antibacterial agents have been suggested in the art to retard plaque formation and the oral infections and dental disease associated with plaque formation. For example, halogenated hydroxydiphenyl ether compounds such as triclosan are well known to the art for their antibacterial activity and have been used in oral compositions to counter plaque formation by bacterial accumulation in the oral cavity. The effectiveness of the antibacterial agent is dependent upon its delivery to and uptake by teeth and soft tissue areas of the gums.

There is therefore a need in the art to provide means whereby the delivery to and uptake by dental tissue of antibacterial compounds contained in oral compositions can be promoted so as to enhance the therapeutic efficacy of the antibacterial agent.

SUMMARY OF THE INVENTION

In accordance with this invention there is provided an oral composition comprising in an orally acceptable vehicle, an effective antiplaque amount of an halogenated diphenyl ether or phenolic antibacterial compound, and an amount of a mixed anionic/zwitterionic surfactant system present at specific weight concentrations in the vehicle effective to increase the delivery and uptake of the antibacterial compound to oral surfaces so as to enhance the therapeutic efficacy of the administered compound.

As will hereinafter be demonstrated, the presence of the mixed surfactant system results in uptake and bioavailability of the antibacterial agent which is unexpectedly higher than for comparable compositions in which the anionic/zwitterionic surfactant system ingredients are outside the scope of the present invention.

DETAILED DESCRIPTION OF THE PREFERRED EMBODIMENTS

The term "oral composition" is used herein to designate products which, in the ordinary course of usage, are retained in the oral cavity for a time sufficient to contact substantially all of the dental surfaces but are not intentionally ingested. Such products include, for example, dentifrices such as toothpaste and gels, mouthwashes, chewing gums and lozenges.

It is essential and critical that the antibacterial containing oral composition of the present invention contain a mixed anionic/zwitterionic surfactant system present at a concentration of about 1.5 to about 4% by weight and preferably about 2 to about 3% by weight wherein the anionic surfactant is the major constituent, the weight concentration being in the range of about 0.5 to about 3.0% by weight and preferably about 1.5 to about 2.50% by weight and the zwitterionic surfactant being present in the oral composition at a concentration of about 0.30 to about 0.1% by weight and preferably about 0.35 to about 0.50% by weight.

Halogenated diphenyl ether antibacterial compounds useful for the preparation of the oral care compositions of the present invention particularly desirable from considerations of antiplaque effectiveness and safety include 2,4,4'-trichloro-2'-hydroxy-diphenyl ether (triclosan) and 2,2'-dihydroxy-5,5'-dibromo-diphenyl ether.

Phenolic compounds useful in the practice of the present invention include phenol and its homologs, mono and polyalkyl and aromatic halophenols, resorcinol and its derivatives and bisphenolic compounds, such phenolic compounds being more fully disclosed in U.S. Pat. No. 5,368,844, the disclosure of which is incorporated herein by reference. Preferred phenolic compounds are n-hexyl resorcinol and 2,2'-methylene bis (4-chloro-6-bromophenol).

The halogenated diphenyl ether or phenolic antibacterial compound is present in the oral composition of the present invention in an effective antiplaque amount, typically about 0.05% to about 2.0% by weight, and preferably about 0.1% to about 1% by weight of the oral composition.

Anionic surfactants useful in the practice of the present invention include the higher fatty acid monoglyceride monosulfates, such as the sodium salts of the monosulfated monoglycerides of hydrogenated coconut oil fatty acid; higher alkyl sulfates, such as sodium lauryl sulfate; higher alkyl aryl sulfonates, such as sodium linear dodecyl benzene sulfonate; higher olefin sulfonates, such as sodium higher olefin sulfonate in which the olefin group is 12 to 21 carbon atoms; higher alkyl alkali sulfoacetates such as sodium lauryl sulfoacetate; higher fatty acid esters of 1,2-dihydroxypropane sulfonates; the substantially saturated higher aliphatic acyl amides of lower aliphatic aminocarboxylic acid alkali metal salts, such as those having 12 to 16 carbon atoms in the fatty acyl radicals; higher alkyl polylower alkoxy (of 10 to 100 alkoxies) sodium sulfates; higher fatty acid sodium and potassium soaps of coconut oil and tallow, and the like. The anionic surfactant, sodium lauryl sulfate, is preferred in the practice of the present invention.

Zwitterionic surfactants useful in the practice of the present invention include betaine compounds such as alkyl amido betaines, alkyl amido propyl betaines, alkyl dimethyl betaines, sulpho betaines and alkyl betaines. The alkyl amido propyl betaine, cocoamido propyl betaine is a preferred zwitterionic surfactant for use in the practice of the present invention.

In the preparation of an oral composition in accordance with the practice of the present invention, an orally acceptable vehicle including a water-phase with humectant is present. The humectant is preferably glycerine, sorbitol, and/or propylene glycol. Water is present typically in amount of at least about 10% by weight, generally about 30 to 60% by weight and the humectant concentration typically totals about 40–60% by weight of the oral composition.

Dentifrice compositions such as toothpastes and gels also typically contain polishing materials including crystalline silica, having a particle size of up to about 20 microns, such as commercially available Zeodent 115, silica gel or colloidal silica, complex amorphous alkali metal aluminosilicates, hydrated alumina, sodium metaphosphate as well as sodium bicarbonate, calcium carbonate, calcium pyrophosphate, dicalcium phosphate and dicalcium phosphate dihydrate. Typically, the polishing material is included in semi-solid or pasty dentifrice compositions of the present invention in an amount of from about 15 to about 60% by weight and preferably from about 20 to about 55%.

Pyrophosphate salts having antitartar efficacy such as a dialkali or tetraalkali metal phosphate salts such as $Na_4P_2O_7$, $K_4P_2O_7$, $Na_2K_2P_2O_7$, $Na_2H_2P_2O_7$ and $K_2H_2P_2O_7$, long chain polyphosphates such as sodium hexametaphosphate and cyclic phosphate such as sodium trimetaphosphate may be incorporated in oral compositions of the present invention preferably at concentration of about 0.5 to about 8.0% by weight and preferably about 0.5 to about 3.0% by weight. In liquid oral preparations, the pyrophosphate salts are incorporated at a concentration of about 0.1 to about 2% by weight.

Dentifrices prepared in accordance with the present invention typically contain a natural or synthetic thickener in proportions of about 0.1 to about 5% by weight, preferably about 0.5 to about 2% by weight. Suitable thickeners include Irish moss, i-carrageenan, gum tragacanth, starch, polyvinylpyrrolidone, hydroxyethypropyl cellulose, hydroxybutyl methyl cellulose, hydroxypropyl methylcellulose, hydroxyethyl cellulose, sodium carboxymethyl cellulose and colloidal silica.

The oral composition may also contain a source of fluoride ions, or fluoride-providing compound, as an anticaries agent, in an amount sufficient to supply about 25 ppm to 5,000 ppm of fluoride ions and preferably 500 to 1500 ppm fluoride ions. Among these compounds are inorganic fluoride salts, such as soluble alkali metal salts, for example, sodium fluoride, potassium fluoride, sodium fluorosilicate, ammonium flourosilicate and sodium monofluorphosphate, as well as tin fluorides, such as stannous fluoride and stannous chloride.

An antibacterial enhancing agent may also be included in the oral composition. The use of antibacterial enhancing agents in combination with antibacterial agents such as triclosan is known to the art, as for example U.S. Pat. No. 5,188,821 and U.S. Pat. No. 5,192,531. Preferably, the antibacterial enhancing agent is an anionic polymeric polycarboxylate having a molecular weight of about 1,000 to about 1,000,000, preferably about 30,000 to about 500,000. Anionic polymeric polycarboxylates are generally employed in the form of their free acids or preferably as a partially or fully neutralized water soluble alkali metal salt, e.g., sodium, potassium or ammonium salts. Preferred antibacterial enhancing agents are 1:4 to 4:1 copolymers of maleic anhydride or acid with another polymerizable ethylenically unsaturated monomer, preferably a methyl vinyl ether/ maleic anhydride copolymer having a molecular weight (M.W.) of about 30,000 to abut 1,000,000, most preferably about 30,000 to about 500,000. These copolymers are available, for example, under the trademark Gantrez, e.g., Gantrez AN 139 (M.W. 500,000), AN 119 (M.W. 250,000); and preferably Gantrez S-97 Pharmaceutical Grade (M.W. 700,000), of GAF Corporation.

The antibacterial enhancing agent is incorporated in the compositions of the present invention in weight amounts of about 0.05 to about 3%, and preferably about 0.1 to about 2%.

Any suitable flavoring or sweetening material may also be employed in the preparation of the oral compositions of the present invention. Examples of suitable flavoring constituents include flavoring oils, e.g. oil of spearmint, peppermint, wintergreen, clove, sage, eucalyptus, marjoram, cinnamon, lemon, orange, and methyl salicylate. Suitable sweetening agents include sucrose, lactose, maltose, xylitol, sodium cyclamate, aspartyl phenyl alanine methyl ester, saccharine and the like. Suitably, flavor and sweetening agents may each or together comprise from about 0.1% to 5% more of the oral composition.

Various other materials may be incorporated in the oral preparations of this invention such as whitening agents, including urea peroxide, calcium peroxide, and hydrogen peroxide, preservatives, vitamins such as vitamin B6, B12, E and K, silicones, chlorophyll compounds and potassium salts for the treatment of dental hypersensitivity such as potassium nitrate and potassium citrate. These agents, when present, are incorporated in the compositions of the present invention in amounts which do not substantially adversely affect the properties and characteristics desired.

The manufacture of the oral composition of the present invention is accomplished by any of the various standard techniques for producing such compositions. To make a dentifrice, a vehicle is prepared containing glycerol, sorbitol, and propylene glycol, thickener agents and antibacterial agent such as triclosan, and the vehicle and a mixture of anionic and zwitterionic surfactants are added, followed by blending in of a polishing agent, as well as any polyphosphate and fluoride salts, with the pre-mix. Finally, flavoring agent, is admixed and the pH is adjusted to between 6.8 to 7.0.

The following examples are further illustrative of the present invention, but it is understood that the invention is not limited thereto. All amounts and proportions referred to herein and in the appended claims are by weight, unless otherwise indicated.

EXAMPLE I

The effect of a mixture of anionic and zwitterionic surfactants when present in an oral composition on the uptake absorption to dental tissue of a halogenated diphenyl ether antibacterial agent was assessed using disks of saliva coated hydroxyapatite (SCHAP), the mineral phase of dental enamel, as an in vitro experimental model for human teeth. The in vitro assessment has been found to be correlatable to in vivo uptake of antibacterial agents on dental tissue surfaces.

In this in vitro assessment, hydroxyapatite (HAP) is washed extensively with distilled water, collected by vacuum filtration, and dried overnight at 37° C. The dried HAP is ground into a powder and 150 milligrams (mgs) of the powder is placed into a chamber of a KBr pellet die (Barnes Analytical, Stanford, Conn.). The HAP powder is compressed for 6 minutes at 10,000 pound in a Carver Laboratory press to prepare 13 mm diameter disks which are sintered for 4 hours at 800° C. in a Thermolyne furnace.

Stimulated saliva was clarified by centrifuging for 10 minutes at 15,000×g. Hydroxyapatite disks were incubated in the clarified saliva overnight in a 37° C. shaking water bath to develop a pellicle.

To determine the delivery of triclosan to a saliva treated hydroxyapatite disk (SCHAP) disk from a dentifrice containing triclosan and 2% weight of an anionic surfactant (sodium lauryl sulphate) were mixed in combination with zwitterionic surfactant cocoaidio propyl betaine of varying concentrations (0 to 0.6% by weight), SCHAP disks were treated with a dentifrice slurry prepared using ingredients from compositions identified in Table I. The amounts of dentifrice slurry used to contact the disks simulated in vivo surface to volume ratios found in the mouth. The dentifrice slurries were a liquid phase solution which contained all the components of a dentifrice except the abrasive. The liquid phase, in part, simulates brushing condition. After incubation for 30 minutes at 37°C., the SCHAP disks were removed from the dentifrice slurry, washed three times with water.

The uptake absorption of Triclosan, on SCHAP disks from these compositions are set forth in Table II below.

TABLE I

| Ingredients | Weight % |
|---|---|
| NaF | 0.320 |
| Na saccharin | 0.300 |
| Glycerin | 15.00 |
| Carboxymethyl cellulose | 0.400 |
| Sorbitol-NC-70% | 42.42 |
| Dye | 0.034 |
| Gantrez | 0.500 |
| NaOH (50%) | 0.500 |
| Silica abrasive | 23.500 |
| Flavor | 1.200 |
| Triclosan | 0.300 |
| Sodium lauryl sulfate | 2.0 |
| Cocoamidio propyl betaine | 0–0.6 |
| Water | Balance |

TABLE II

| Cocoamidio Propyl Betaine Concentration Wt. % | Triclosan Uptake (ppm) |
|---|---|
| 0 | 56.5 |
| 0.25 | 82.3 |
| 0.30 | 97.5 |
| 0.35 | 106.8 |
| 0.40 | 140.6 |
| 0.50 | 105.5 |

EXAMPLE II

The procedure of Example I was repeated except a series of dentifrice compositions was prepared containing Triclosan and an anionic/zwitterionic surfactant system containing 0.4% cocoamido propyl betaine in which the sodium lauryl sulfate concentration was varied from 0 to 4% by weight. The ingredients of this dentifrice composition are recorded in Table III below. The uptake absorption of Triclosan on SCHAP disks from these compositions are recorded in Table IV below.

TABLE III

| Ingredients | Weight % |
|---|---|
| NaF | 0.320 |
| Na saccharin | 0.300 |
| Glycerin | 15.000 |
| Thickener | 0.400 |
| Sorbitol-NC-70% | 42.42 |
| Dye | 0.034 |
| Triclosan | 0.3 |
| Silica abrasive | 23.500 |
| Flavor | 1.200 |
| Sodium lauryl sulfate | 0–3.5 |
| Cocoamidio propyl betaine | 0.40 |
| Water | Balance |

TABLE IV

| Sodium Lauryl Sulfate Concentration Wt. % | Triclosan Uptake (ppm) |
|---|---|
| 0 | 8.8 |
| 1.0 | 73.6 |
| 1.5 | 86.2 |
| 1.75 | 89.9 |
| 2.0 | 96.5 |
| 2.25 | 97.7 |
| 2.50 | 98.0 |
| 3.00 | 91.9 |

The results recorded in Tables II and IV show that uptake of Triclosan on SCHAP disks from dentifrice compositions containing 0.3 to 0.4% by weight of the zwitterionic surfactant cocoamidiopropyl betaine and 2.0 to 3% by weight of the anionic surfactant sodium lauryl sulfate was significantly enhanced as compared to the use of mixed surfactant systems of identical surfactants outside these concentration ranges.

What is claimed is:

1. An oral composition exhibiting increased uptake by dental tissue of antibacterial compounds contained therein, the composition consisting essentially of an orally acceptable vehicle, an effective therapeutic amount of a halogenated diphenyl ether or phenolic antibacterial compound and a mixture of anionic and zwitterionic surfactants, the antibacterial agent being incorporated in the composition at a concentration of about 0.05 to about 2.0% by weight, the anionic surfactant being present in the composition at a concentration of about 2 to 3% by weight and the zwitterionic surfactant being present in the composition at a concentration of about 0.3 to 0.4% by weight.

2. The composition of claim 1 wherein the antibacterial agent is Triclosan.

3. The composition of claim 1 wherein the anionic surfactant is sodium lauryl sulfate.

4. The composition of claim 1 wherein the zwitterionic surfactant is a cocoamido propyl betaine.

5. A method for the treatment and prevention of bacterial plaque accumulation on teeth which comprises administering to the oral cavity an oral composition comprising an orally acceptable vehicle consisting essentially of an effective therapeutic amount of a halogenated diphenyl ether or phenolic antibacterial compound and a mixture of anionic and zwitterionic surfactants, the antibacterial compound exhibiting increased uptake to dental tissue, the antibacterial agent is incorporated in the composition at a concentration of about 0.05 to about 2.0% by weight, the anionic surfactant being present in the composition at a concentration of about 2 to 3% by weight and the zwitterionic surfactant being present in the composition at a concentration of about 0.3 to 0.4% by weight.

6. The method of claim 5 wherein the antibacterial agent is Triclosan.

7. The method of claim 5 wherein the anionic surfactant is sodium lauryl sulfate.

8. The method of claim 5 wherein the zwitterionic surfactant is a cocoamido propyl betaine.

* * * * *